US009783445B1

United States Patent
Cole et al.

(10) Patent No.: US 9,783,445 B1
(45) Date of Patent: Oct. 10, 2017

(54) METHOD, SYSTEM, AND EQUIPMENT FOR GLASS MATERIAL PROCESSING AS A FUNCTION OF CRYSTAL STATE

(71) Applicant: Corning Incorporated, Corning, NY (US)

(72) Inventors: Sara Ann Cole, Corning, NY (US); Galan Gregory Moore, West Henrietta, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/221,060

(22) Filed: Jul. 27, 2016

Related U.S. Application Data

(60) Provisional application No. 62/350,399, filed on Jun. 15, 2016.

(51) Int. Cl.
*C03B 5/24* (2006.01)
*C03B 5/235* (2006.01)

(52) U.S. Cl.
CPC ............. *C03B 5/24* (2013.01); *C03B 5/235* (2013.01)

(58) Field of Classification Search
None
See application file for complete search history.

(56) References Cited

U.S. PATENT DOCUMENTS

| | | | | |
|---|---|---|---|---|
| 3,975,177 A | * | 8/1976 | Masuda | C03B 18/02 65/158 |
| 7,304,310 B1 | * | 12/2007 | Shortt | G01N 21/94 250/372 |
| 2002/0109110 A1 | * | 8/2002 | Some | G01N 21/9501 250/559.4 |
| 2010/0226524 A1 | * | 9/2010 | Shakespeare | G01N 21/47 382/100 |
| 2012/0025112 A1 | * | 2/2012 | Li | G01F 23/292 250/577 |
| 2014/0263970 A1 | * | 9/2014 | Heimbuch | G01J 1/0411 250/208.2 |

OTHER PUBLICATIONS

Volkov et al., "Automated Multichannel System for In-line Monitoring of Float-Glass Ribbon Thickness in the Hot Zone of an Annealing Furnace", Glass and Ceramics, vol. 65, Nos. 5-6, 2008, pp. 144-147.*

(Continued)

*Primary Examiner* — Lisa L Herring
(74) *Attorney, Agent, or Firm* — Russell S. Magaziner

(57) ABSTRACT

A method of processing a glass material includes guiding and/or focusing light from a light source to glass material in a hot stage of a processing system, where the light source provides light at a wavelength λ that interacts with crystals that may be formed in the glass material. The method includes collecting and/or guiding light directed from the glass material in the hot stage to a wavelength separator, and separating the light directed from the glass material to provide a spectrum δ having wavelengths that are within about twenty nanometers of the wavelength λ. The method includes observing with a detector light of the spectrum δ to identify nano-scale shifts in the wavelength λ caused by interaction with crystals, if present, within the glass material in the hot stage of the processing system.

6 Claims, 3 Drawing Sheets

(56) References Cited

OTHER PUBLICATIONS

Khalili, "Development, Implementation and Validation of In-Situ Raman Hot Stage Reactor", Dept. of Chemical and Material Engineering, University of Alberta, 2014, 98 pages—hereinafter Khalili.*

Harvey, Analytical Chemistry 2.0—Chapter 10: Spectroscopic Methods, https://www.saylor.org/site/wpcontent/uploads/2012/07/Chapter1011.pdf, pp. 543-645, Wayback Machine date Aug. 2013.*

LaPlant, "Laser, Spectrographs, and Detectors", Engineering Raman Applications and Techniques in Biomedical and Pharmaceutical Fields, Springer, 2010, pp. 1-24.*

Khan et al., In-situ Raman spectroscopy and X-ray diffraction studies of the structural transformations leading to the SrCu2O2 phase from strontium-copper oxide thin films deposited by metalorganic chemical vapor deposition, Thin Solid Films, Nov. 2012, pp. 136-141.*

Tempco, "Tempco Flexible Heaters" Catalogue, http://www.tempco.com/Catalog/Section%209-pdf/Heating%20Tape.pdf, available online Oct. 28, 2015 per WaybackMachine, 5 pages.*

Clegg et al.; "On-Line Analysis Using Raman Spectroscopy for Process Control during the Manufacture of Titanium Dioxide"; Applied Spectroscopy, vol. 55, No. 9 (2001); pp. 1138-1150.

Guimbretiere et al,; "In-Situ Raman Observation of the First Step of Uranium Dioxide Weathering Exposed to Water Radiolysis" Spectr. Lett. 44 (2011); pp. 570-573.

Grimaud et al.; "Transport properties and in-situ Raman spectroscopy study of $BaCe0.9Y0,1O3-ö$ as a function of water partial pressures"; Solid State Ionics 191 (2011); pp. 24-31.

Dutreilh-Colas et al,; "In-situ Raman diagnostic of structural relaxation times of silica glasses" J. Am. Ceram. Soc. 94 (2011); pp. 2087-2091.

Canizares et al.; "In-Situ Raman Monitoring of $UO(2)/H(2)O$ Interfaces Under $He(2+)$ Irradiation"; AIP Conference Proceedings 1267, 790 (2010); pp. 790-791.

Particle Analytical "Hot Stage Microscopy (non-GMP)"; copyright 2016; Retrieval Date: Jan. 16, 2017; http://particle.dk/methods-analytical-laboratory/hot-stage-microscopy/.

* cited by examiner

METHOD, SYSTEM, AND EQUIPMENT FOR GLASS MATERIAL PROCESSING AS A FUNCTION OF CRYSTAL STATE

This application claims the benefit of priority under 35 U.S.C. §119 of U.S. Provisional Application Ser. No. 62/350,399, filed on Jun. 15, 2016, the content of which is relied upon and incorporated herein by reference in its entirety.

BACKGROUND

In general, sensors and instrumentation are used to monitor and improve the quality of glass material processing. Thermometers measure temperature in different locations throughout processing equipment. Strain gauges, load cells, and pressure sensors may also be incorporated in processing equipment. Glass products are then manufactured by monitoring and reacting to information from sensors and instrumentation throughout processing.

Scientific techniques to measure actual microstructure, nanostructure, local surface, etc., are generally unsuited for implementation within glass processing equipment. Temperatures are too high. As a result, conventional processing of glass materials typical relies on "recipes" (i.e. temperature schedules, compositions, environmental conditions, etc.) that have been empirically developed to produce glass materials having certain attributes, such as optical clarity, high strength, flexibility, toughness, etc. Instrumentation allows operators to follow the recipes.

However, recipes and measured parameters only provide estimates as to actual microstructure and molecular interactions and states within glass materials during processing. As a result, manufacturers may process glass materials with higher margins for error in terms of temperature, cycle time, etc., possibly increasing temperatures in a furnace well above temperatures actually needed, for example; and as a result, sometimes end products lack desired attributes and need to be thrown out or corresponding processes waste energy and time. A need exists to improve efficiency and predictability in processing of glass materials.

SUMMARY

Aspects of the present disclosure relate generally to processing (e.g., manufacturing, strengthening, researching) glass materials, such as glass and/or glass-ceramics. More specifically, aspects of the present disclosure relate to equipment and methods for processing glass materials as a function of crystal state or crystal growth in the glass materials during processing in hot stages of equipment.

Applicants have discovered a system to determine crystallization activity in glass material while the glass material is hot, which allows operators of the processing equipment (e.g., human operator, computerized controller) to adjust or tune temperatures or other aspects in the processing equipment to achieve a desired state of crystallization in the glass material, such as presence of crystals of a particular phase, a certain percentage crystal content, fully amorphous, etc. as the glass material is being processed, thereby improving efficiency and reducing chances of error.

Some embodiments relate to a method of processing a glass material, which includes steps of guiding and/or focusing light from a light source to glass material in a hot stage of a processing system, where the light source provides light at a wavelength $\lambda$ that interacts with crystals that may be formed in the glass material. The method includes steps of collecting and/or guiding light directed from the glass material in the hot stage to a wavelength separator, and separating the light directed from the glass material to provide a spectrum $\delta$ having wavelengths that are within about twenty nanometers of the wavelength $\lambda$. The method includes observing with a detector the spectrum $\delta$.

Applicants have discovered that focusing attention on a narrow spectrum $\delta$ immediately surrounding wavelength $\lambda$ may be performed even when glass material is at high temperature, which may be counterintuitive to scientists relying on absence of light (i.e. absorption) because of large amount of infrared interference and noise associated with high temperatures. Instead, Applicants use the detector to search for nano-scale shifts or scattering of the light in the wavelength $\lambda$ caused by interaction with crystals, if present, within the glass material in the hot stage of the processing system. Applicants believe that the nano-scale shifts or scattering correspond to vibration, rotation, and/or low-frequency modes of the glass material on a molecular level, and thus provide crystallization information to Applicants to guide processing.

The above method may further include changing conditions in the hot stage as a function of the crystallization information. For example, changing conditions may more specifically include changing temperature in the hot stage by at least 10° Celsius in response to the crystallization information. In some such embodiments, the method may include growing crystals in the glass material, and concluding thermal treatment of the glass material in the hot stage based on the crystallization information.

In some contemplated embodiments, the system further comprises a computerized controller in communication with the detector, where the above-described step of changing conditions in the hot stage is automated by the computerized controller. In some embodiments, the method includes filtering out light directed from the glass material at the wavelength $\lambda$, such as to better observe light shifted or scattered about the wavelength $\lambda$. The step of guiding and/or focusing light may further include directing the light from the light source through an access port in the hot stage.

Other embodiments relate to systems and equipment that may facilitate such processing.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE FIGURES

The accompanying Figures are included to provide a further understanding, and are incorporated in and constitute a part of this specification. The drawings illustrate one or more embodiments, and together with the Detailed Description serve to explain principles and operations of the various embodiments. As such, the disclosure will become more fully understood from the following Detailed Description, taken in conjunction with the accompanying Figures, in which.

DETAILED DESCRIPTION

Before turning to the following Detailed Description and Figures, which illustrate exemplary embodiments in detail, it should be understood that the present inventive technology is not limited to the details or methodology set forth in the Detailed Description or illustrated in the Figures. For example, as will be understood by those of ordinary skill in the art, features and attributes associated with embodiments shown in one of the Figures or described in the text relating to one of the embodiments may well be applied to other embodiments shown in another of the Figures or described elsewhere in the text.

Figure 1:
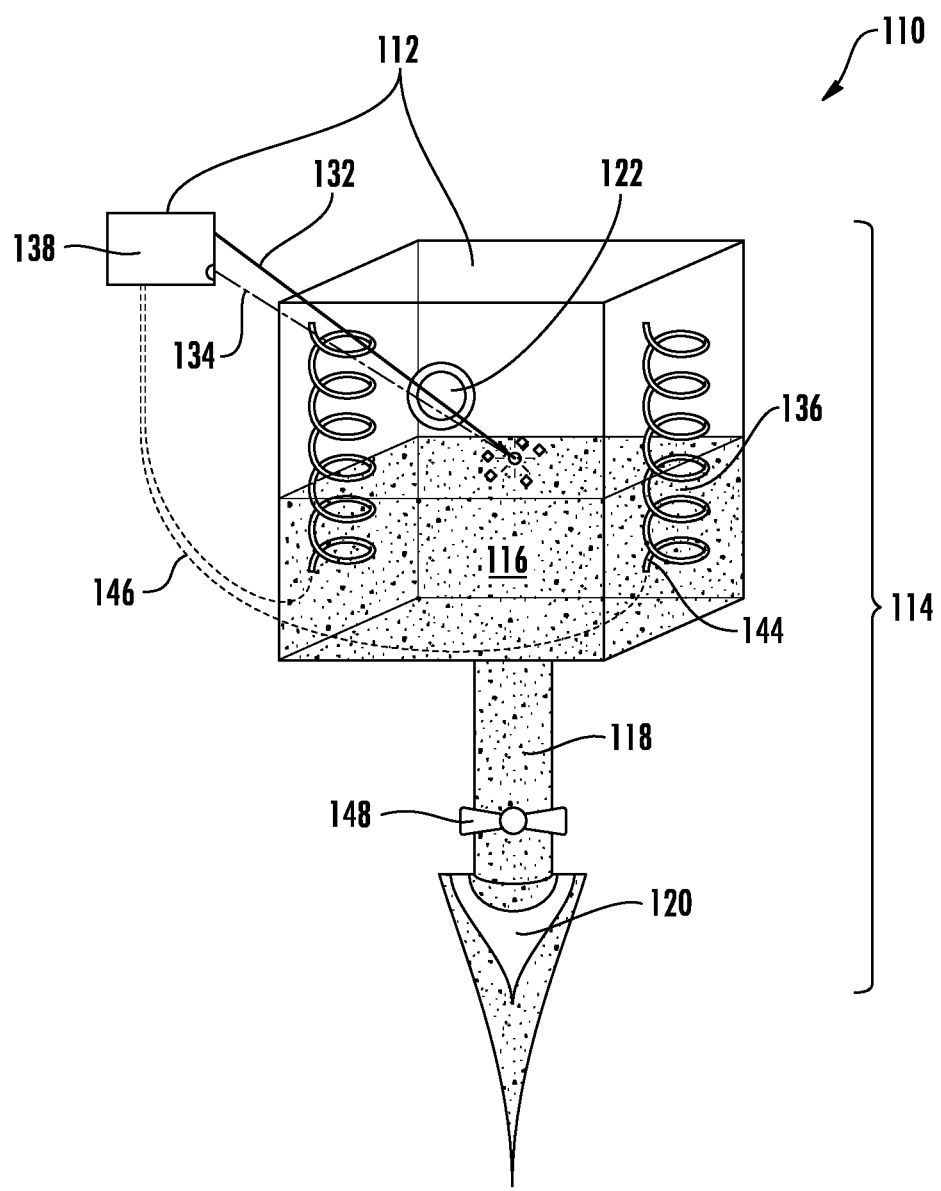
FIG. 1 is a conceptual representation of a system for processing glass material according to an exemplary embodiment.

Referring to FIG. 1, a system 110 for processing glass material 116 includes equipment 112 including a hot stage 114. According to various exemplary embodiments, the system 110 may be a commercial manufacturing line or a portion thereof for producing glass products, such as glass sheets; a research rig for testing new glass formulations or otherwise analyzing glass; or another such system for processing glass materials 116. According to an exemplary embodiment, the system 110 is or is part of a fusion draw for processing glass material. In other embodiments, the system 110 is or is part of a float process for processing glass material. In still other embodiments, system 110 is or is part of a furnace or oven for heat treating glass materials, such as to facilitate controlled crystallization in the glass materials.

Figure 2:
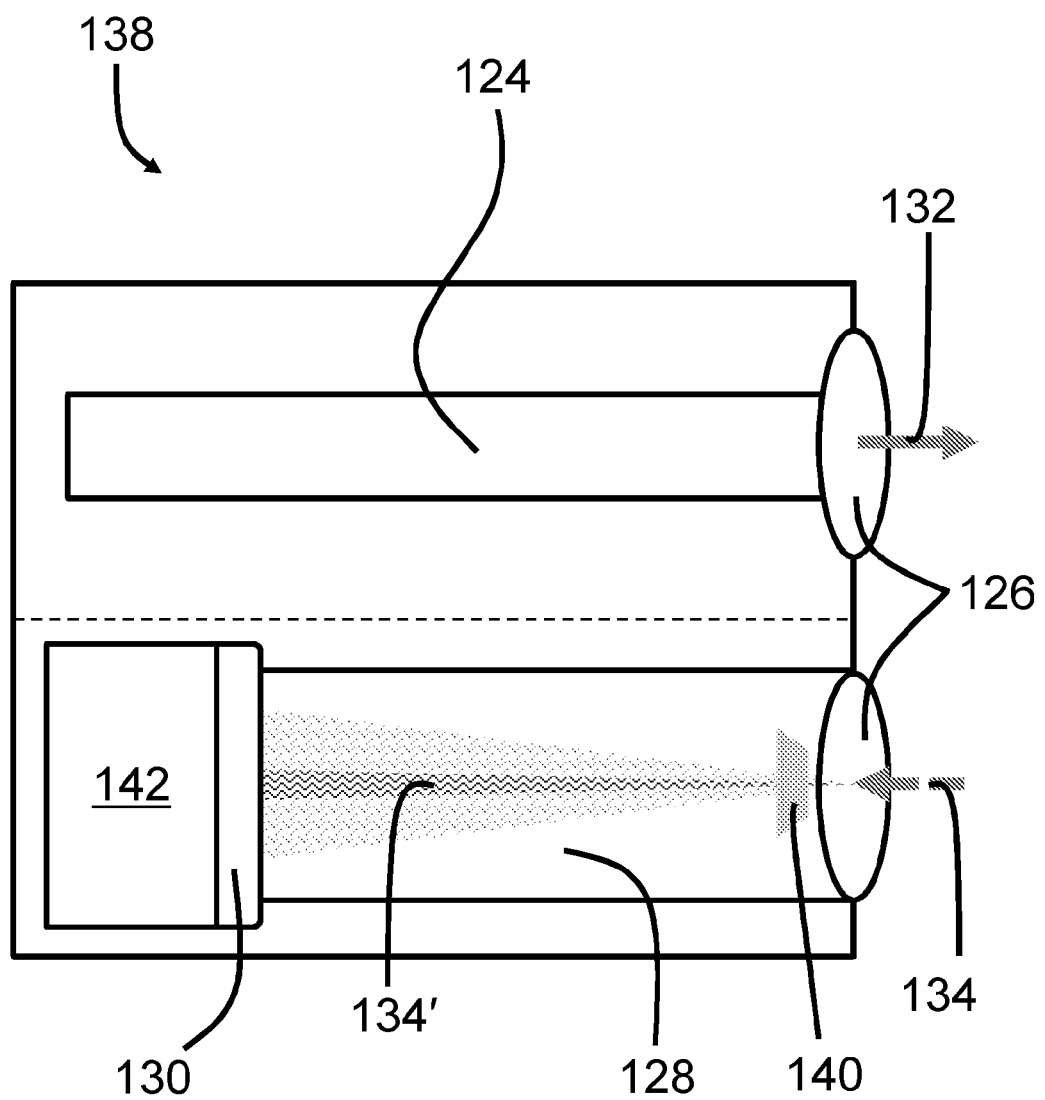
FIG. 2 is a conceptual representation of components of the system of FIG. 1.

According to an exemplary embodiment and also referring to FIG. 2, the system 110 further includes a light source 124, optics 126, a wavelength separator 128, and a detector 130. The light source 124 provides a light 132 (e.g., beam) at a wavelength λ that is directed to the glass material 116 in the hot stage 114. If present, crystals in the glass material 116 may scatter the light 132, returning, emitting, or reflecting light 134 in a spectrum δ indicative of properties of the crystals, such as vibrational characteristics thereof. As shown in FIGS. 1-2, at least some of the light 134 is received by the wavelength separator 128 by way of the optics 126, which focus a desired portion 134' of that light on the detector 130.

Crystallization information (i.e., information related to crystal content of the glass material 116, such as crystal state, crystal phase, pre-crystal clustering, crystal structure, location of crystals, size, amount of crystal content, amount of crystals of a certain phase, lack of crystals, etc.) from the detector 130 may be useful for an operator of the system 110 to efficiently operate the system 110, as discussed herein.

In one exemplary scenario, a glass manufacturer may be manufacturing sheets of glass that the manufacturer desires to be completely amorphous. The manufacturer may be operating the glass processing equipment 112 according to a temperature schedule believed to facilitate the completely amorphous end product. However, a system of the present disclosure, according to an exemplary embodiment, may detect clustering of glass materials on a micro- or even nano-scale, which may be an early indication of crystallization. In such a scenario, the operator of the equipment 112 may then raise the temperature, such as by at least ten degrees Celsius, of the processing equipment 112, such as in a hot stage 114 corresponding to a location of clustering or up-stream thereto, to improve sheet quality.

In another representative scenario, a glass manufacturer may be manufacturing articles of glass-ceramic to have a particular concentration of a certain crystal phase. A temperature schedule or "recipe" may be used to achieve such a concentration, based on empirical data from previous manufacturing. However, a system of the present disclosure, according to another exemplary embodiment, may be used to precisely determine when the desired crystal concentration is present, possibly allowing the operator of the equipment to conclude, complete, or shut down the crystallization process sooner, and thus reducing the time and heat energy required to achieve the desired glass-ceramic end-product articles.

In still another contemplated scenario, a glass manufacturer may be developing a "recipe" for a new glass and/or glass-ceramic product, such as one that has a particular and/or unique crystal structure: for example, a sheet with layers of different crystal phases or discrete areas of different crystal concentrations. Such a recipe may require complicated and precise changing or control of temperature and/or other parameters, such as vacuum pressure, gas type, sonic energy, light intensity/frequency, deposition timing, etc. Development of such a recipe may be time consuming and costly using conventional practices. However, a system of the present disclosure, according to another exemplary embodiment, may be used to monitor and determine real-time when desired intermediate properties in a glass and/or glass ceramic are present, allowing the operator of the corresponding equipment to change to the next step of processing.

As indicated above, glass material 116, as used herein, refers to glass-ceramic having crystals formed therein and/or glass that may form crystals therein. Exemplary glass materials include LAS-System materials (i.e., mixtures of lithium-, aluminum-, and silicon-oxides that may further include glass-phase forming agents such as $Na_2O$, $K_2O$, and CaO and/or refining agents; e.g., $Li_2O \times Al_2O \times nSiO_2$-System), MAS-System materials (e.g., $MgO \times Al2O_3 \times nSiO_2$-System), ZAS-System (e.g., $ZnO \times Al_2O_3 \times nSio_2$), chalcogenide glass (e.g., AgInSbTe and GeSbTe), silicate glasses such as soda-lime glass, fused silica, sodium borosilicate, lead-oxide glass, aluminosilicate glass, oxide glass, ULE® (ultra-low expansion glass). Such glass materials may be tempered, ion-exchanged, or otherwise modified.

The hot stage 114 (e.g., hot zone, hot area, heated stage, high-temperature portion) of the system 110 may be or include a furnace 136, a hot section 118, an isopipe 120, a muffle, a melter, and/or another high temperature section of equipment. In some embodiments, the equipment 112 may include some, but not all of the components shown in FIG. 1, such as including a furnace 136 and heated section 118, but no isopipe 120 for example. According to an exemplary embodiment, the hot stage 114 is at least partially surrounding the glass material 116 and/or is configured to at least partially surround the glass material 116, and/or to at least partially contain, support, fully surround the glass material 116. In some embodiments, temperatures in the hot stage 114, such as temperatures of the glass materials 116 in the hot stage 114, exceed 200° C., such as exceeding 400° C., 500° C., or even higher and/or no greater than 3000° C., such as no greater than 2000° C.

In some embodiments, temperatures in the hot stage 114, such as temperatures of the glass materials 116 in the hot stage 114, may be within 400° C. of a melting temperature of the glass material 116, such as within 300° C., within 200° C., or within 100° C.; and/or no more than 1000° C. greater than the melting temperature of the glass material 116, such as no more than 500° C. greater, no more than 200° C. greater, no more than 100° C. greater than the melting temperature of the glass material 116. In other such embodiments, temperatures in the hot stage 114, such as temperatures of the glass materials 116 in the hot stage 114, may be within 400° C. of a glass transition temperature of glass material 116 in the hot stage 114, such as within 300° C., within 200° C., or within 100° C.; and/or no more than 1000° C. greater than the glass transition temperature of glass material 116 in the hot stage 114, such as no more than 500° C. greater, no more than 200° C. greater, no more than 100° C. greater than the glass transition temperature of the glass material 116. In still other embodiments, temperatures in the hot stage 114, such as temperatures of the materials in the hot stage 114, are within such above-described temperature ranges of a sintering temperature of materials in the hot stage 114. Having the temperatures in the hot stage 114 be in close proximity to critical temperatures of the glass material 116 in the hot stage 114, as disclosed herein and quantified above, may be particularly efficient, saving energy to heat the hot stage 114 and/or facilitating desired properties or qualities in the glass material 116 being processed by the system 110. However, without live or real-time crystallization information, such close or low temperatures may be too risky for conventional glass processing, such as due to risk of inadvertent crystallization.

In some embodiments the light source 124 is a laser. In other embodiments, the light source 124 is a halogen light source. According to an exemplary embodiment, the system 110 includes the light source 124 that provides the light 132 at a particular wavelength λ selected to interact with crystals that may be formed in the glass material 116. According to an exemplary embodiment, the wavelength λ of the light 132 is ultraviolet, near ultraviolet, visible, near infrared, infrared, and/or is a wavelength λ within a subset of such ranges of the electromagnetic spectrum, such as within the near ultraviolet (e.g., wavelength from 10 nm to 380 nm), visible (e.g., wavelengths from about 390 to 700 nm), and/or near infrared (e.g., wavelength 700 nanometers to 1 mm). In some embodiments, the wavelength λ of the light 132 is about 532 nm, about 193 nm, about 266 nm, about 488 nm, about 514 nm, or another value.

In some embodiments, the light 132 may be generally monochromatic, such as at least 95% of corresponding light energy within a 5 nm band around wavelength λ, at least 95% of corresponding light energy within a 2 nm band around wavelength λ, and/or at least 99% of corresponding light energy within a 5 nm band around wavelength λ. In some such embodiments, the light source 124 and corresponding light 132 with wavelength λ is selected to generate, in the glass material 116, spectral contributions of shifted spectral bands of amorphous and/or crystalline states of the glass material 116, while mitigating effects on the glass material 116 due to wavelength-induced changes to the glass material 116 caused by the light 132, such as fluorescence, absorption, etc.

According to an exemplary embodiment, equipment 138, such as the light source 124 and/or other equipment, is located or positioned outside of the hot stage 114, allowing the equipment 138 to be separated or shielded from heat of the hot stage 114. In some such embodiments, the hot stage 114 has an access port, window, opening, etc., such as an optical access port 122. The access port 122 allows or facilitates transmission of the light 132 from the light source 124 to the material 116 at least partially surrounded by the hot stage 114. In other contemplated embodiments, an access port may be in the form of an optical fiber that extends into the hot stage 114, allowing some or all of equipment 138 (FIG. 2) to be operated outside of the hot stage 114. In some embodiments, the light source 124 is exterior to the hot stage 114 such that a temperature on equipment 138 of the light source 124 is at least one-hundred degrees Celsius less than a temperature of the glass material 116 in the hot stage 116.

According to an exemplary embodiment, light 134 is received by the wavelength separator 128, where the light 134 may pass out of the access port 122, directed from the glass material 116. The wavelength separator 128 may be or include a spectrometer, a filter, a prism, a grating, multiple or combinations of such components and/or other componentry to isolate or select light 134' of interest. In some such embodiments, the wavelength separator 128 sends, directs, or otherwise provides light of interest 134' to the detector 130.

According to an exemplary embodiment, the detector 130 may be used in the system 110 to observe light wavelengths (or wavenumber) of the light of interest 134'. Put another way, the detector 130 is set to receive a portion 134' of light 134 separated by the wavelength separator 128, the portion 134' of light 134 being within a range of about ±20 nm of the wavelength λ of the light 132 that the light source 124 provides (i.e., within twenty nanometers of wavelength λ or within about 420 wavenumbers of wavelength k), such as within 15 nm of k, such as within about 2100 wavenumbers (e.g., 2100±400 wavenumbers) of wavelength k. Observation of this particular subset of light may be useful to observe nano-scale shifts in the wavelength λ of the light 132 from the light source caused by interaction of the light 132 from the light source 124 with crystals of the glass material 116, such as so-called inelastic or Raman scattering. Some exemplary detectors may be or include photo-multiplier tubes, charged couple devices (CCD) and variants thereof (e.g., ICCD, EMCCD, etc.), and photo-diodes.

According to an exemplary embodiment, optics 126 may be used by the system 110 to guide and/or focus light 132 from the light source 124 into the hot stage 114 and onto the glass material 116 at least partially surrounded by the hot stage 114, and to collect and/or guide scattered light 134 from the glass material 116 at least partially surrounded by the hot stage 114 and direct the light 134 to the wavelength separator 128. Some exemplary optics 126 may be or include lenses, mirrors, microscope objectives, filters, and beam splitters, for example. The optics 126 may have different functions in the system 110, such as focusing a beam, collecting scattered light, etc. and those functions may be filled by one or more separate optics elements. In some embodiments, the optics 126 include a filter 140, such as a notch filter, edge pass filter, or a band pass filter for filtering out light of the spectrum δ that is at the wavelength λ.

In some embodiments, an operator of the system 110 may use data, information, etc. from the detector 130 to control operation of the system 110, such as to change temperature of the furnace 136 by at least 10° Celsius within 10 minutes of receiving the information, such as by at least 50° Celsius, 100° Celsius, 300° Celsius, such as to stop a heat treatment when a certain crystal content is present.

In some embodiments, the operator is a computerized controller 142, where the computerized controller 142 changes conditions in the hot stage as a function of information from the detector 130. For example, the system 110 in FIG. 1 shows the equipment 138, which may include the computerized controller 142, to be in electronic communication with heating elements 144 on the furnace, such as via wires 146. The computerized controller 142 may be programmed to hold a temperature until a desired crystal state (e.g., amount, phase, concentration) is present in the glass material 116.

Using the presently disclosed technology, thermal treatment time may be reduced relative to that provided by conventional processes because the operator may know, through direct observation, when a desired crystal state is present, as opposed to waiting a period of time based on a thermal schedule that includes a margin for error or 'factor of safely.' In some embodiments, the operator may control other aspects of the system as a function of crystal state in the glass material 116. For example, valve 148 may be controlled as a function of crystal state in the glass material 116, not opening until the glass material 116 is fully amorphous.

Figure 3:
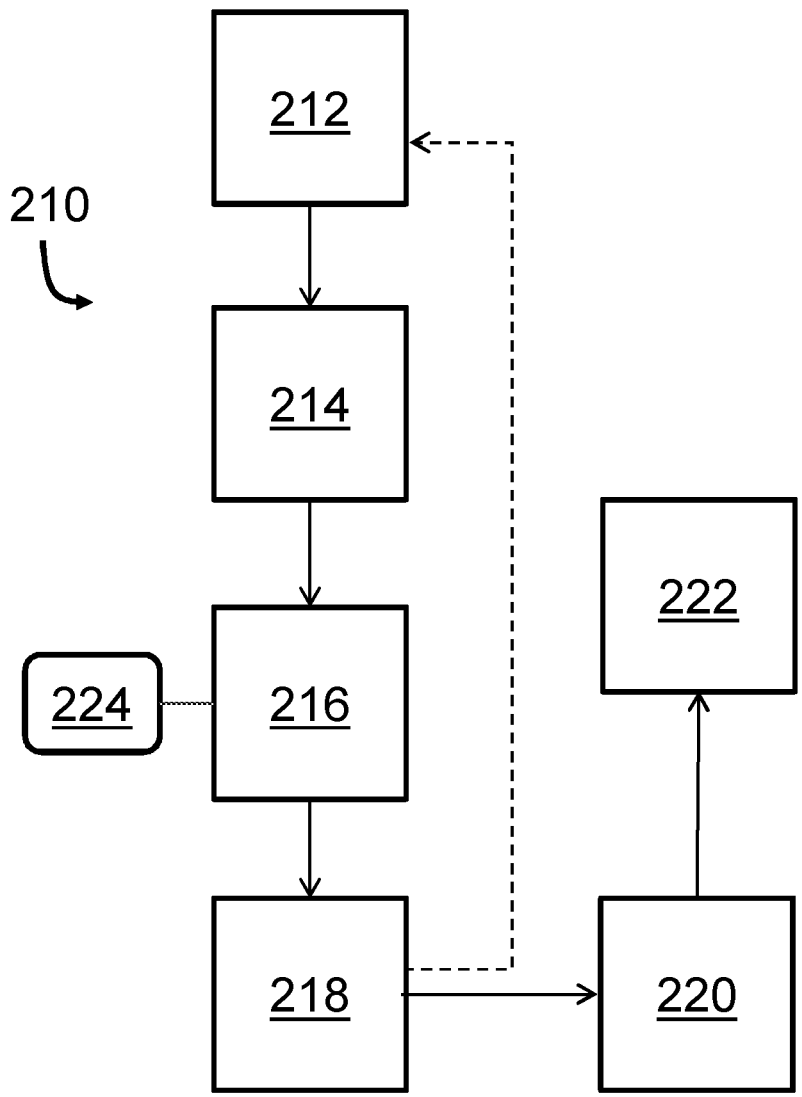
FIG. 3 is a flow chart diagram of a method of processing according to an exemplary embodiment.

Referring now to FIG. 3, some embodiment relate to a method of processing, such as a method for processing a glass material 210 that includes guiding and/or focusing 212 light 132 from a light source 124 to glass material 116 in a hot stage 114 of a processing system 110, where the light source 124 provides light 132 at a wavelength $\lambda$ that interacts with crystals that may be formed in the glass material 116. The method 210 includes collecting and/or guiding 214 light 134 directed from the glass material 116 in the hot stage 114 to a wavelength separator 128, and separating the light 134 directed from the glass material 116 to provide a spectrum $\delta$ having wavelengths that are within about twenty nanometers of the wavelength $\lambda$. The method 210 includes observing 216 with a detector 142 the spectrum $\delta$, in search of nano-scale shifts in the wavelength $\lambda$ caused by interaction with crystals, if present, within the glass material 116 in the hot stage 114 of the processing system 110.

The method 210 may further include changing 218 conditions in the hot stage 114 as a function of crystallization information 224 from the detector 142. For example, the changing 218 conditions may more specifically include changing temperature in the hot stage 114 by at least 10° Celsius in response to the crystallization information 224, as disclosed above. In some such embodiments, the method 210 may include growing crystals 220 in the glass material 116, and concluding 222 thermal treatment of the glass material 116 in the hot stage 116 based on the crystallization information 224. In some such embodiments, the glass material 116 is a glass-ceramic and the method 210 further comprises changing 218 temperatures in the hot stage to facilitate growth of crystals in the glass material 116 based on the crystallization information 224. In some contemplated embodiments, the system 110 further comprises a computerized controller 142 in communication with the detector 130, where the above-described step of changing 218 conditions in the hot stage 114 is automated by the computerized controller 142.

In some embodiments, the separating 216 includes filtering out a portion of light 134 directed from the glass material 116 at the wavelength k. The guiding and/or focusing 212 light 132 further includes directing the light 132 from the light source 124 through an access port 122 in the hot stage 114. The method 210 and steps thereof may be modified to include the details disclosed herein pertaining to the system 110 and related equipment 112. Further, any of the steps or sequences of the method 210 may be recursive, as suggested by the dotted line connecting steps 218 and 212 for example, such as to achieve intermediate conditions or attributes when processing glass materials 116. Further, embodiments of methods disclosed herein include methods without some steps shown in FIG. 3, such as a method for manufacturing an amorphous glass may not include the growing 220 step, but may include the concluding step 222 or the concluding step may be replaced by opening the valve 148. The changing 218 step may be changing a condition other than temperature, such as pressure, constituent content, adding nucleation agents, opening a valve, changing a flow rate, or another condition of processing.

The construction and arrangements of the methods, systems, and equipment, as shown in the various exemplary embodiments, are illustrative only. Although only a few embodiments have been described in detail in this disclosure, many modifications are possible (e.g., variations in sizes, dimensions, structures, shapes, and proportions of the various elements, values of parameters, mounting arrangements, use of materials, colors, orientations) without materially departing from the novel teachings and advantages of the subject matter described herein. For example, in at least some contemplated embodiments, the system disclosed herein may be used with materials that are not glass, such as for processing inorganic materials, organic materials, ceramics, polymers, gem stone materials (e.g., peridot, opal, sapphire, garnet, etc.), etc. In some contemplated embodiments, Applicants may use above disclosed equipment and steps to search for absorption of infrared light in the glass materials, such as in lower-temperature processing (e.g., less than 1000° Celsius and/or at least 200° Celsius). Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present inventive technology.

What is claimed is:

1. A system for glass material processing, comprising:
   glass material comprising glass-ceramic having crystals formed therein;
   a hot stage heated by heating elements at least partially surrounding the glass-ceramic;
   a light source that provides light at a wavelength $\lambda$ that interacts with the crystals formed in the glass-ceramic;
   a wavelength separator that separates out a spectrum $\delta$ of light from the glass-ceramic that is within a range of ($\lambda$−20 nm) to ($\lambda$+20 nm);
   a detector that is set to receive light of the spectrum $\delta$ of light from the wavelength separator;
   optics that guide and/or focus light from the light source to the glass-ceramic in the hot stage, and that collect and/or guide light directed from the glass-ceramic in the hot stage and direct the light directed from the glass-ceramic to the wavelength separator, wherein the optics at least in part prevent the detector from receiving light at the wavelength $\lambda$; and
   a computerized controller, where the computerized controller is in electronic communication with the heating elements of the hot stage and facilitates a control loop between the heating elements and the detector where the computerized controller changes conditions in the hot stage as a function of information derived from the detector such that at least some of the glass-ceramic is at a temperature no more than 500° C. greater than a glass transition temperature of glass material in the hot stage.

2. The system of claim 1, wherein the wavelength λ of the light is in the near ultraviolet or visible range of the electromagnetic spectrum.

3. The system of claim 1, wherein the information comprises crystal state, crystal phase, pre-crystal clustering, crystal structure, location of crystals, size, amount of crystal content, and/or amount of crystals of a certain phase.

4. A system for glass material processing, comprising:
glass material comprising glass-ceramic having crystals formed therein;
a hot stage heated by heating elements at least partially surrounding the glass-ceramic, wherein at least some of the glass-ceramic is at a temperature of at least 500° C.;
a light source that provides light at a wavelength λ that interacts with the crystals formed in the glass-ceramic, wherein at least 95% of light energy from light of the light source is within a 5 nm band around wavelength λ thereby facilitating spectral contributions of shifted spectral bands of crystalline states of the glass material, while mitigating effects on the glass material due to wavelength-induced changes to the glass material caused by the light;
a wavelength separator that separates out a spectrum δ of light from the glass-ceramic that is within a range of (λ−20 nm) to (λ+20 nm);
a detector that is set to receive light of the spectrum δ of light from the wavelength separator;
optics that guide and/or focus light from the light source to the glass-ceramic in the hot stage, and that collect and/or guide light directed from the glass-ceramic in the hot stage and direct the light directed from the glass-ceramic to the wavelength separator, wherein the optics at least in part prevent the detector from receiving light at the wavelength λ, thereby focusing the detector on nano-scale shifted light within the spectrum δ; and
a computerized controller, where the computerized controller is in electronic communication with the heating elements of the hot stage and facilitates a control loop between the heating elements and the detector where the computerized controller changes conditions in the hot stage as a function of information derived from the detector such that at least some of the glass-ceramic is at a temperature no more than 500° C. greater than a glass transition temperature of glass material in the hot stage.

5. The system of claim 4, wherein the wavelength λ of the light is in the near ultraviolet or visible range of the electromagnetic spectrum.

6. The system of claim 5, wherein the wavelength λ of the light is about 532 nm, about 193 nm, about 266 nm, about 488 nm, or about 514 nm.

* * * * *